United States Patent [19]
Bueno et al.

[11] Patent Number: 6,127,418
[45] Date of Patent: Oct. 3, 2000

[54] GABA ANALOGS TO PREVENT AND TREAT GASTROINTESTINAL DAMAGE

[75] Inventors: Lionel Bueno, Aussonne; Maria Chovet, Montrouge; Laurent Diop, Saclay, all of France; Antonio Guglietta, Ann Arbor, Mich.; Hilary J. Little, County Durham, United Kingdom; Michael Francis Rafferty, Ann Arbor, Mich.; Jiayuan Ren, Oklahoma City, Okla.; Charles Price Taylor, Jr., Chelsea, Mich.; William P. Watson, Meadowfield, United Kingdom

[73] Assignee: Warner-Lambert Company, Morris Plains, N.J.

[21] Appl. No.: 09/284,710

[22] PCT Filed: Aug. 18, 1998

[86] PCT No.: PCT/US98/17082

§ 371 Date: Apr. 19, 1999

§ 102(e) Date: Apr. 19, 1999

[87] PCT Pub. No.: WO99/08671

PCT Pub. Date: Feb. 25, 1999

Related U.S. Application Data

[60] Provisional application No. 60/074,794, Feb. 16, 1998, and provisional application No. 60/056,753, Aug. 20, 1997.

[51] Int. Cl.[7] ................................................. A61K 31/195
[52] U.S. Cl. ............................................................ 514/561
[58] Field of Search ............................................. 514/561

[56] References Cited

FOREIGN PATENT DOCUMENTS

96/11680   4/1996   WIPO .
98/11885   3/1998   WIPO .
98/17627   4/1998   WIPO .

OTHER PUBLICATIONS

PCT International Search Report, PCT/US98/17082.

Lesch, et al. *Gastroenterology*, The GABA–Derivative 3–Isobutyl GABA Acts Centrally to Protect Against Indomethacin–Induced Gastric Damage in Rats, vol. 114, No. 4, 1998, p. 200 XP002081396.

Ren, et al., *Gastroenterology*, Effects of Gabapentin on Indomethacin–induced and Ethanol–Induced Gastric Injury, vol. 114, No. 4, 1998, p. 267, XP002081397.

Watson, et al., *Neuropharmacology*, The Novel Anticonvulsant, Gabapentin, Protects Against both Convulsant and Anxiogenic Aspects of the Ethanol Withdrawal Syndrome, vol. 36, No. 10, pp. 1369–1375, 1997.

*Primary Examiner*—Raymond Henley, III
*Attorney, Agent, or Firm*—Charles W. Ashbrook

[57] ABSTRACT

The present invention is directed to a method for preventing visceral and gastrointestinal damage such as gastric ulcers by administering a gamma-aminobutyric acid (GABA) analog and for treating gastrointestinal diseases such as inflammatory bowel disorders (IBD), functional bowel disorders (FBD) including dyspepsia and other visceral pain.

27 Claims, 9 Drawing Sheets

FIG-6 Gabapentin and Naproxen Mixtures Show Synergy in Rat Carrageenan Footpad Thermal Hyperalgesia FIG-7 Gabapentin and Naproxen Mixtures Show Synergy in Rat Carrageenan Footpad Thermal Hyperalgesia

GABA ANALOGS TO PREVENT AND TREAT GASTROINTESTINAL DAMAGE

This application claims priority under 35 U.S.C. 119(e) over provisional applications 60/074,794 filed Feb. 16, 1998 and 60/056,753 filed Aug. 20, 1997, and is a 371 of PCT/US98/17082 filed Aug. 18, 1998.

FIELD OF THE INVENTION

This invention relates to a method for preventing visceral and gastrointestinal damage such as gastric ulcers by administering a gamma-aminobutyric acid (GABA) analog, and for treating gastrointestinal diseases such as inflammatory bowel disorders (IBD), functional bowel disorders (FBD), including dyspepsia and other visceral pain.

BACKGROUND OF THE INVENTION

Nonsteroidal anti-inflammatory drugs (NSAIDs) are the most frequently prescribed drugs for the treatment of pain associated with osteoarthritis and many other musculoskeletal and inflammatory disorders. In the United States, about 100 million prescriptions are written each year to provide effective relief of pain and treatment of inflammatory diseases. Commonly used NSAIDs include sulindac, naproxen, indomethacin, mefenamic acid, diclofenac, fenoprofen, and diflunisal.

However, considerable evidence indicates that NSAIDs have frequent, serious, and costly gastrointestinal tract toxic side effects. These include mild dyspepsia, gastritis, peptic ulcer disease, as well as more serious gastrointestinal complications such as bleeding and perforation, leading sometimes to significant morbidity and, to a lesser extent, mortality. Serious GI complications due to NSAID use represent the greatest threat to life in patients with connective tissue diseases, second only to the primary disease and its complications. Similar gastrointestinal damage is caused by ingestion of alcohol. Indeed, a condition known as ethanol withdrawal syndrome is commonly encountered when prolonged ethanol consumption is terminated. In addition to gastrointestinal damage, this syndrome often results in tremors, anxiety, convulsions, hallucinations, and confusion.

Other commonly encountered gastrointestinal disorders include inflammatory bowel disorders (IBD) and functional bowel disorders (FBD), including dyspepsia. These GI disorders include a wide range of disease states that are currently only moderately controlled, including Crohn's disease, ileitis, ischemic bowel disease, and ulcerative colitis, as well as IBD, the irritable bowel syndrome, dyspepsia, and gastro-esophageal reflux for FBD, and other forms of visceral pain.

Gamma-aminobutyric acid has been shown to activate gastric afferent nerves which, in turn, have been shown to participate in gastric defense mechanisms. We have now discovered that GABA analogs dramatically reduce the gastrointestinal damage caused by drugs and alcohol. The GABA analogs also treat the conditions resulting from ethanol withdrawal syndrome, and GI disorders characterized as IBD and IBS.

All that is required to prevent gastrointestinal damage and to treat IBD, IBS, and alcoholism according to this invention is to administer to a subject who is in need of treatment an effective amount of a GABA analog.

Several GABA analogs are known. Gabapentin, a cyclic GABA analog, is now commercially available and extensively used clinically for treatment of epilepsy and neuropathic pain. Such compounds are described in U.S. Pat. No. 4,024,175. Another series of GABA analogs which are anti-seizure agents is described in U.S. Pat. No. 5,563,175.

SUMMARY OF THE INVENTION

This invention provides a method for preventing and treating gastrointestinal damage and disorders comprising administering to a subject in need of treatment an effective amount of a GABA analog. A preferred embodiment utilizes a cyclic amino acid compound of Formula I wherein $R_1$ is hydrogen or lower alkyl and n is an integer of from 4 to 6, and the pharmaceutically acceptable salts thereof. An especially preferred embodiment utilizes a compound of Formula I where $R_1$ is hydrogen and n is 5, which compound is 1-(aminomethyl)-cyclohexane acetic acid, known generically as gabapentin. Other preferred GABA analogs have Formula I wherein the cyclic ring is substituted, for example with alkyl such as methyl or ethyl. Typical compounds include (1-aminomethyl-3-methylcyclohexyl)acetic acid, (1-aminomethyl-3-methylcyclopentyl)acetic acid, and (1-aminomethyl-3,4-dimethylcyclopentyl)acetic acid.

In another embodiment, the method of the invention utilizes a GABA analog of Formula II or a pharmaceutically acceptable salt thereof, wherein
$R_1$ is a straight or branched alkyl of from 1 to 6 carbon atoms, phenyl, or cycloalkyl of from 3 to 6 carbon atoms;
$R_2$ is hydrogen or methyl; and
$R_3$ is hydrogen, methyl, or carboxyl.

Diastereomers and enantiomers of compounds of Formula II can be utilized in the invention.

An especially preferred method of the invention employs a compound of Formula II where $R_2$ and $R_3$ are both hydrogen, and $R_1$ is —$(CH_2)_{0-2}$–i $C_4H_9$ as an (R), (S), or (R,S) isomer.

A more preferred embodiment of the invention utilizes 3-aminomethyl-5-methyl-hexanoic acid, and especially (S)-3-(aminomethyl)-5-methylhexanoic acid, now known generically as pregabalin, as well as CI-1008. Another preferred compound is 3-(1-aminoethyl)-5-methylhexanoic acid.

The invention additionally provides a composition comprised of an anti-inflammatory amount of an NSAID and a cytoprotective amount of a GABA analog.

DETAILED DESCRIPTION OF THE INVENTION

As noted above, the method of this invention utilizes any GABA analog. A GABA analog is any compound derived from or based upon gamma-aminobutyric acid. The compounds are readily available, either commercially, or by synthetic methodology well-known to those skilled in the art of organic chemistry. The preferred GABA analogs to be utilized in the method of this invention are cyclic amino acids of Formula I. These are described in U.S. Pat. No. 4,024,175, which is incorporated herein by reference. Another preferred method utilizes the GABA analogs of Formula II, and these are described in U.S. Pat. No. 5,563,175 which is incorporated herein by reference.

All that is required to practice the method of preventing and treating gastrointestinal damage and disorders of this invention is to administer a GABA analog in an amount that is effective to prevent or treat the damage condition, i.e., to combat the effects of a NSAID or alcohol, or to control IBD and IBS. The invention includes a method for treating ethanol withdrawal syndrome and general alcoholism. The effective amount of GABA analog to be utilized will generally be from about 1 to about 300 mg per kg of subject body weight. Typical doses will be from about 10 to about 5000 mg per day for an adult subject of normal weight.

Typical "gastrointestinal damage" conditions caused by NSAID use include dyspepsia, gastritis, peptic ulcer, as well as lower gastrointestinal bleeding and perforation. Further effects of ethanol withdrawal syndrome include tremor, anxiety, and convulsions. Typical IBD conditions include ileitis, ulcerative colitis, and Crohn's disease.

Pharmaceutical compositions of the compound of the present invention or its salts are produced by formulating the active compound in dosage unit form with a pharmaceutical carrier. Some examples of dosage unit forms are tablets, capsules, pills, powders, aqueous and nonaqueous oral solutions and suspensions, and parenteral solutions packaged in containers containing either one or some larger number of dosage units and capable of being subdivided into individual doses. Some examples of suitable pharmaceutical carriers, including pharmaceutical diluents, are gelatin capsules; sugars such as lactose and sucrose; starches such as corn starch and potato starch, cellulose derivatives such as sodium carboxymethyl cellulose, ethyl cellulose, methyl cellulose, and cellulose acetate phthalate; gelatin; talc; stearic acid; magnesium stearate; vegetable oils such as peanut oil, cottonseed oil, sesame oil, olive oil, corn oil, and oil of theobroma; propylene glycol, glycerin; sorbitol; polyethylene glycol; water; agar; alginic acid; isotonic saline, and phosphate buffer solutions; as well as other compatible substances normally used in pharmaceutical formulations. The compositions of the invention can also contain other components such as coloring agents, flavoring agents, and/or preservatives. These materials, if present, are usually used in relatively small amounts. The compositions can, if desired, also contain other therapeutic agents. For use in combating the gastrointestinal effects of NSAIDs, the GABA analogs can be administered alone in unit dosage form, or in combination with the NSAID being utilized for the particular patient.

The percentage of the active ingredient in the foregoing compositions can be varied within wide limits, but for practical purposes it is preferably present in a concentration of at least 10% in a solid composition and at least 2% in a primary liquid composition. The most satisfactory compositions are those in which a much higher proportion of the active ingredient is present, for example, from 10% to 90% by weight.

Routes of administration of the subject compound or its salts are oral or parenteral. For example, a useful intravenous dose is between 5 and 50 mg and a useful oral dosage is between 20 and 800 mg. The dosage is within the dosing range used in treatment of gastrointestinal diseases such as ulcers and IBS, or as would be dictated by the needs of the patient as described by the physician.

A unit dosage form of the GABA analog to be used in this invention may also comprise other compounds useful in the therapy of gastrointestinal diseases.

The advantages of using the compounds of Formula I and II, especially gabapentin and pregabalin, in the instant invention include the relatively nontoxic nature of the compounds, the ease of preparation, the fact that the compounds are well-tolerated, and the ease of IV and oral administration of the drugs. Further, the drugs are not metabolized in the body to any great extent.

The subjects as used herein are mammals, including humans.

The invention also provides a composition comprising an NSAID (non-steroidal anti-inflammatory drug) together with a GABA analog. The NSAID will be present in an anti-inflammatory amount, preferably somewhat less than normally used, and the GABA analog will be present in a cytoprotective amount, namely an amount which will be effective in preventing or reducing the gastrointestinal damage otherwise caused by the NSAID. In general, the NSAID will be present for doses of about 10 to about 500 mg, and the GABA analog will be present at about 1 to about 1500 mg. Any NSAID can be combined with any GABA analog according to this invention. Preferred GABA analogs to be employed are the compounds of Formulas I and II, especially gabapentin and pregabalin. Preferred NSAIDs to be employed in the compositions include sulindac, naproxen, indomethacin, mefenamic acid, diclofenac, fenoprofen, diflunisal, etodolac, ibuprofen, piroxicam, acetylsalicylic acid, oxaprozin, and bromfenac. Most of the NSAIDs to be used are commercially available, generally as salts such as calcium, sodium, or potassium, for example, fensprofen calcium and bromfenac sodium. Especially preferred combinations include pregabalin or gabapentin, together with naproxen sodium or ibuprofen. The compositions may contain common pharmaceutical excipients such as those described above.

The ability of GABA analogs to treat gastrointestinal diseases according to this invention has been established in several animal models of induced gastric lesions and alcoholism.

EXAMPLE 1

Gabapentin was evaluated in animals to determine its ability to prevent gastric lesions otherwise caused by indomethacin.

Male Sprague-Dawley rats weighing 240 to 250 g were fasted for 24 hours and allowed free access to water prior to experiment. All test drugs were given intragastrically. Rats were pretreated with different doses of gabapentin at doses of 40 and 60 mg. Thirty minutes later indomethacin (25 mg/kg) was administered. Another group of rats received 10 mg of gabapentin twice, 3 hours apart, followed by indomethacin administration. Three hours after indomethacin treatment, the rats were killed and gastric lesions were assessed. The severity of the lesions were determined by the measurement of the square area (mm$^2$) of visible lesions.

Results

1. Indomethacin caused severe gastric hemorrhagic injury; the areas of injury were measured at 42.6±5.2 mm$^2$ (mean,±standard error of mean).

2. Gabapentin pretreatment significantly reduced indomethacin-induced gastric injury. The gastric lesion with different doses of gabapentin pretreatment after indomethacin treatment were measured: 22.3±2.8 mm$^2$ with 40 mg, 16.5±2.2 mm$^2$ with 60 mg/kg, and 4.2±0.39 mm$^2$ with 10 mg twice.

3. Gabapentin pretreatment also dramatically reduced gastric bleeding.

Figure 1:
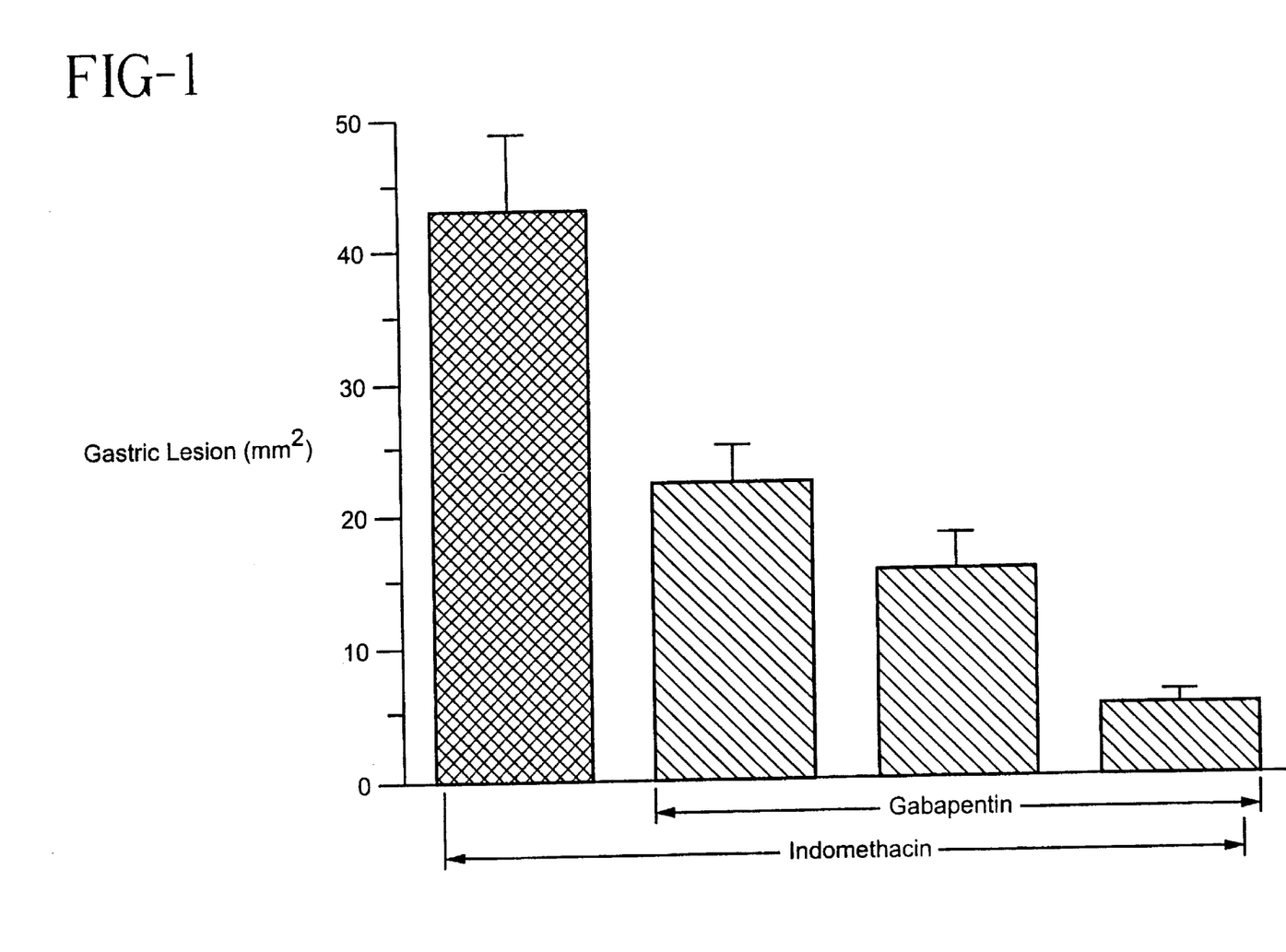
FIG. 1 shows the effect of gabapentin on gastric lesions caused by indomethacin.

The foregoing data are presented in FIG. 1, where the first bar is control (animals treated with indomethacin alone); Bar 2 is for animals treated with one dose of 40 mg of gabapentin; Bar 3 is for animals dosed one time with 60 mg of gabapentin; and Bar 4 is for animals dosed two times with 10 mg of gabapentin.

EXAMPLE 2

To determine the effects of gabapentin on ethanol-induced gastric lesions, rats were pretreated with 1 mL of 70% aq. ethanol (v/v), followed by gabapentin at a dose of 40 and 60 mg, respectively. Another group of rats were pretreated by 20 mg of gabapentin given twice, 3 hours apart, followed by ethanol administration. Thirty minutes later, all rats were killed and gastric lesions were assessed.

Results

1. Seventy percent ethanol induced significant gastric injury. The area of injury measured 41.9±3.7 mm$^2$.

2. Gabapentin pretreatment reduced ethanol-induced gastric injury. With 2 doses of 20 mg gabapentin pretreatment, the area of injury measured 2.1±0.3 mm$^2$. With 40 and 60 mg of gabapentin pretreatment, the area of injury measured 24.4±3.5 mm$^2$ and 18.7±2.2 mm$^2$, respectively.

EXAMPLE 3

The following test in rats was carried out to further establish the ability of gabapentin and Pregabalin to reduce the gastrointestinal damage caused by NSAIDS.

Animals

Male CD-Sprague-Dawley rats (132–202 g) were received and housed in a room with controlled temperature, humidity, and 12-hour light/dark cycle. After a period of acclimatization of 4 to 5 days, and after a 24-hour food fasting period, animals were used for the study described below.

Administration of GABA Analogs and Indomethacin

Gabapentin or pregabalin (CI-1008) were dissolved in water and administered orally at the following doses: 1, 10, 100, and 200 mg/kg in a volume of 1 mL. Control animals were dosed with an equal volume of vehicle (1 mL of water). Sixty minutes later, all the animals received 1 mL of a solution of indomethacin dissolved in 5% aqueous NaHCO$_3$ (80 mg/kg). Control animals received 1 mL of 5% aqueous NaHCO$_3$ orally. Experimental groups were as follows:

| Group | Pretreatment | Damaging Agent |
|---|---|---|
| Group 1 | Water | None (NaHCO$_3$) |
| Group 2 | Water | Indomethacin 80 mg/kg |
| Group 3 | Gabapentin 1 mg/kg | Indomethacin 80 mg/kg |
| Group 4 | Gabapentin 10 mg/kg | Indomethacin 80 mg/kg |
| Group 5 | Gabapentin 100 mg/kg | Indomethacin 80 mg/kg |
| Group 6 | Gabapentin 200 mg/kg | Indomethacin 80 mg/kg |
| Group 7 | Pregabalin 1 mg/kg | Indomethacin 80 mg/kg |
| Group 8 | Pregabalin 10 mg/kg | Indomethacin 80 mg/kg |
| Group 9 | Pregabalin 100 mg/kg | Indomethacin 80 mg/kg |
| Group 10 | Pregabalin 200 mg/kg | Indomethacin 80 mg/kg |

Evaluation of the Effect

Gastric damage caused by indomethacin correlates with inhibition of the cyclooxygenase product prostaglandin E2 (PGE$_2$). Animals were sacrificed by decapitation 4 hours post-indomethacin administration. The stomach was removed and opened along the greater curvature and its image digitized and stored on an optical disk using a 486-based PC computer equipped with CUE3 system imaging analysis software (Olympus Corp., Marietta, Ga., USA). Two 6-mm biopsies were taken from a constant region of the gastric mucosa located in each side of the glandular portion of the stomach, and their PGE$_2$ content was measured using a commercially available ELISA kit (Assay Designs Inc., Ann Arbor, Mich., USA). The presence of gastric damage was determined using the retrieved electronic image, and the extent of damage was measured using the CUE3 imaging software. Data are expressed as a percent of gastric area damaged and the PGE$_2$ content (pg/mL). The data are present below in Table 1.

TABLE 1

| Compound | Drug Dose | N | % Area Damaged | PGE$_2$ Synthesis (pg/mL) |
|---|---|---|---|---|
| Control | NA | 10 | 0.00 ± 0.00* | 9525.27 ± 156.00* |
| Indomethacin ± Vehicle | NA | 9 | 5.56 ± 0.48 | 1908.03 ± 72.31 |
| Indomethacin ± Gabapentin | 1 mg/kg | 5 | 2.99 ± 0.46 | 1783.66 ± 73.47 |
| Indomethacin ± Gabapentin | 10 mg/kg | 9 | 3.96 ± 0.35 | 3065.78 ± 137.19 |
| Indomethacin ± Gabapentin | 100 mg/kg | 10 | 1.87 ± 0.1 | 2997.90 ± 226.80 |
| Indomethacin ± Gabapentin | 200 mg/kg | 5 | 1.43 ± 0.40 | 2615.74 ± 165.36 |
| Indomethacin ± CI-1008 | 1 mg/kg | 4 | 8.07 ± 2.19 | 1209.95 ± 105.50 |
| Indomethacin ± CI-1008 | 10 mg/kg | 10 | 4.07 ± 0.42 | 2666.16 ± 307.45 |
| Indomethacin ± CI-1008 | 100 mg/kg | 10 | 1.99 ± 0.25* | 3994.45 ± 318.95 |
| Indomethacin ± CI-1008 | 200 mg/kg | 5 | 0.34 ± 0.06* | 3288.92 ± 407.43 |

Values are average ± standard error.
*p < 0.05 based on Kruskal-Wallis one-way analysis of variance followed by Dunn's test and compared to indomethacin group.

Both gabapentin and CI-1008 caused a reduction of the amount of gastric damage induced by indomethacin which, in the case of CI-1008, reached statistical significance at doses of 100 and 200 mg/kg.

As expected, the gastric damage caused by indomethacin was associated with a significant inhibition of the cyclooxygenase product PGE$_2$. Neither gabapentin nor CI-1008, at any dose tested, were able to significantly modify this effect. This data suggests that the significant reduction of the indomethacin-induced gastric damage caused by CI-1008 is not related to an effect of this GABA analog on the cyclooxygenase enzyme.

The foregoing data establish that GABA analogs such as gabapentin and pregabalin are effective in preventing gastrointestinal damage such as gastric lesions, peptic ulcers, and even lower gastrointestinal bleeding, otherwise caused by consumption of alcohol or NSAIDs. The GABA analogs also treat the effects of alcohol withdrawal, which is a syndrome characterized by tremor, hallucinations, and confusion, and general gastrointestinal disorders such as IBD and IBS.

The following tests establish that GABA analogs are useful to treat ethanol withdrawal syndrome.

EXAMPLE 4

Male albino mice of the outbred TO strain (Bantin and Kingman, UK) were used in all studies. The weight ranged from 25 to 35 g, with no more than a 5 g range in any single experiment. The mice were housed, eight per cage, at 21° C.±1° C., with 55±10% relative humidity, and a 12-hour light/dark cycle with the light phase between 09:00 to 21:00. All mice received ad libitum access to tap water and standard laboratory chow (RM-1, Special Diet Services, UK) until their use in experiments or until their diet was replaced with a liquid diet.

Induction of Physical Dependence

Ethanol was administered in a liquid diet schedule. All mice received control diet for an initial 2-day period. Ethanol treated mice then received a diet containing 3.5% (v/v) ethanol/water for 2 days, followed by a diet containing 7% ethanol for a further 5 days. The average intake was 22 to 30 g/kg/day. Control groups were pair-fed a control diet, balanced isocalorifically to match the ethanol containing diet. There were no differences in the weights of the ethanol-treated and control mice at the end of the treatment periods. When mice were withdrawn from the ethanol (between 07:00 AM and 09:00 AM), they were provided with tap water until their use in experiments.

Drug Treatment

Gabapentin was dissolved in saline, the solution being made freshly each testing day. Intraperitoneal (i.p.) injections of either gabapentin, 10 mL/kg, or saline, were given immediately on withdrawal from the ethanol treatment in the studies on the handling responses, and 2 hours prior to measurement of audiogenic seizures. In the experiments using a standard elevated plus maze, gabapentin or saline was injected i.p. at 8 hours after the removal of the ethanol diet, and the mice were placed on the plus maze 60 minutes after the injections. In the studies on motor co-ordination (ataxia) and on locomotor activity, gabapentin or saline was injected into ethanol-naive chow fed mice immediately before testing. Measurements were then made for 60 minutes for the ataxia study, and for 30 minutes in the case of the locomotor activity.

Measurement of Handling-Induced Behavior

Following withdrawal from the ethanol treatment at 09:00 AM, ratings of handling-induced behavior were assessed by the same experimenter, on the same mice, every hour for a period of 12 hours after withdrawal from ethanol. Numerical ratings have the definitions shown in Table 2.

TABLE 2

Behavioral Ratings During Gentle Handling

| | |
|---|---|
| 1 | Mild tremor on lifting and turning |
| 2 | Continuous severe tremor on lifting and turning |
| 3 | Clonic forelimb extensor spasm on lifting |
| 4 | Clonic forelimb extensor spasm on lifting, which continued after placing mouse on cage top |
| 5 | Spontaneous evidence of myoclonic activity followed by (4) |

Figure 2A:
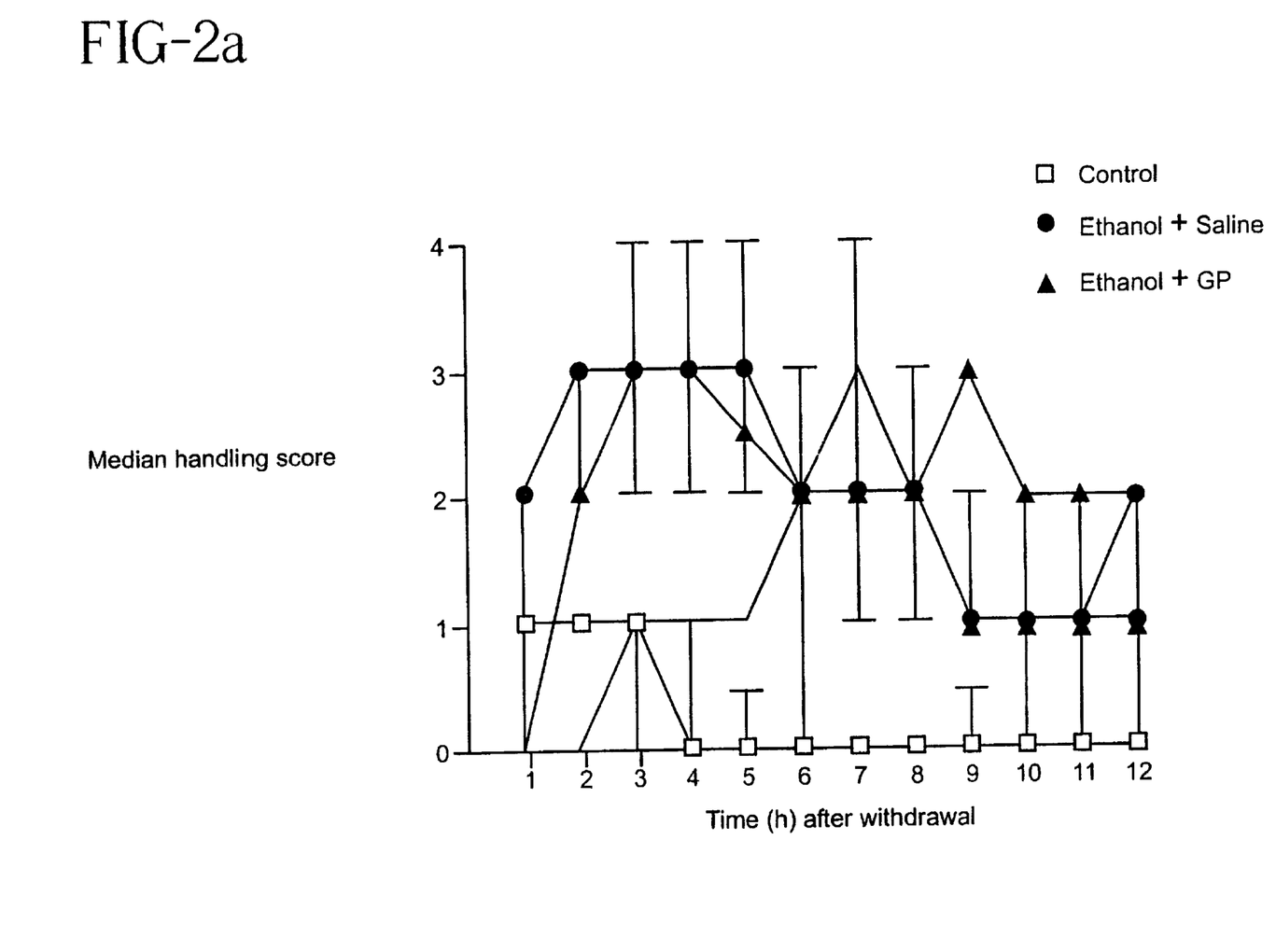
FIG. 2 shows the effect of gabapentin on handling responses following withdrawal of chronic ethanol treatment.
Figure 2B:
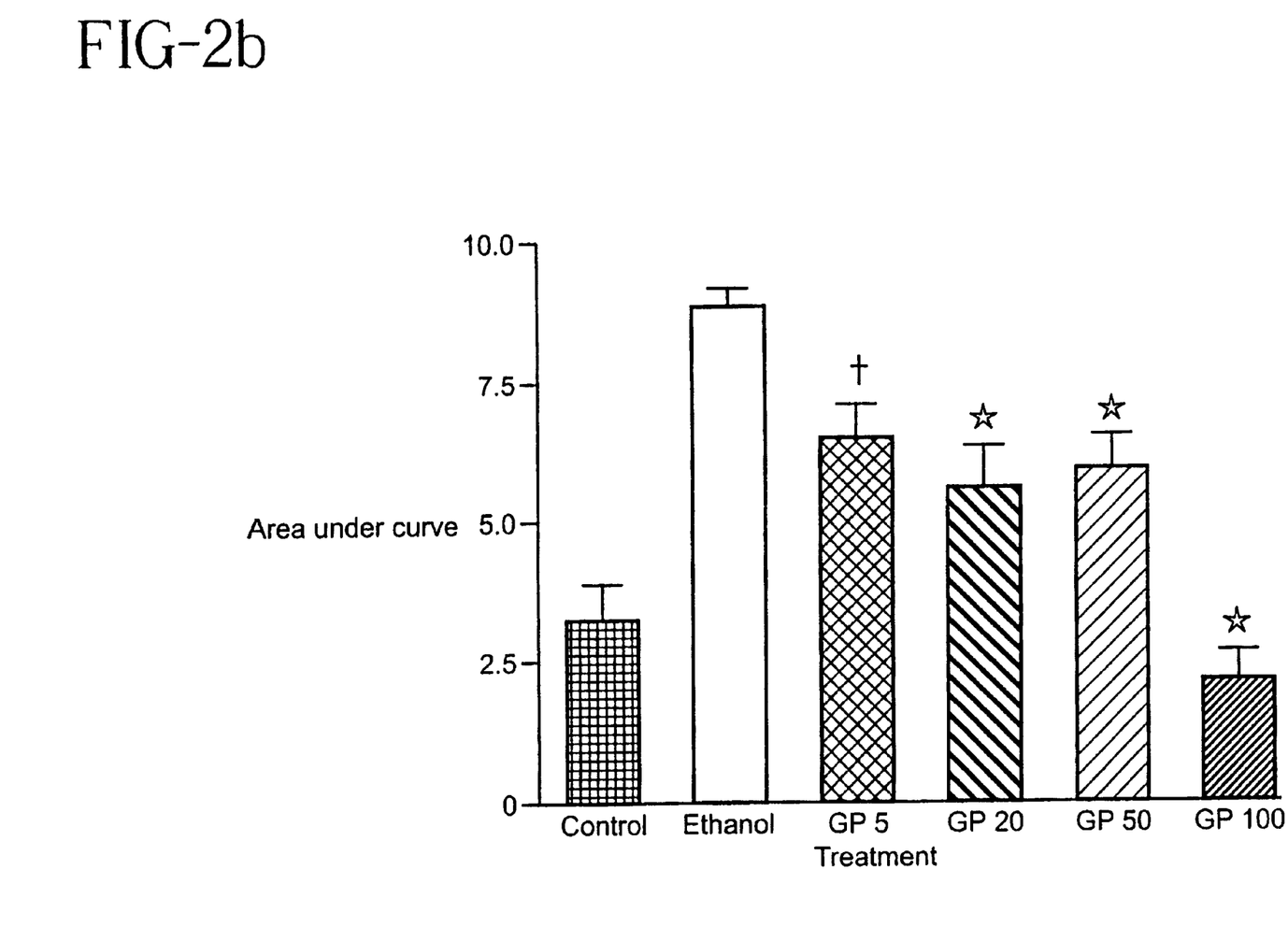

Each mouse was lifted gently by the tail and held for 3 seconds, 30 cm under an "Anglepoise lamp" with a 60-watt bulb. The animal was gently rotated and its ensuing behavior rated on a scale of 1 to 5 according to the criteria in Table 2. Groups of 15 mice were used in each of the treatment groups, and the data were calculated as medians with interquartile ranges. The data were also expressed as the area under the curve at 4 and 12 hours from the withdrawal of the ethanol treatment. The results are shown in FIG. 2.

Elicitation of Audiogenic Seizures

At 8 and 12 hours from ethanol withdrawal, the susceptibility to sound-induced convulsions was measured in separate groups of ten mice. Mice were tested individually in a sound-proof perspex box 30×30×30 cm containing an electric door-bell. The bell was rung for 2 minutes or until the first signs of convulsions. The number of mice which responded by wild-running and clonic convulsions was counted. The mice were humanely killed as soon as a full convulsion was seen.

Anxiety-Related Behavior

Mice were withdrawn from the ethanol diet at 7:00 AM and tested for anxiety-related behavior 8 hours later using a murine elevated plus-maze. It was constructed of perspex with two opposing open arms (30×5×0.25 cm) and two opposing closed arms (30×5×15 cm) which extended from a central platform (5×5 cm). The floor was of matt black perspex. The animals were acclimatized to the experimental room 1 hour prior to experimentation. Experiments were conducted under dim red light, and each 5 minute session was video-taped for later analysis, by an observer unaware of the prior treatment. During this analysis (Observer 3.0, Noldus Information Technology, Wageningen, Netherlands) measurements were made of the time spent on each arm of the maze, the number of entries onto each arm and rearing activity. The measurements were made in accordance with the definitions in Table 3.

TABLE 3

Measurements of Behavior on the Elevated Plus Maze

Arm entry = All four paws onto either a closed or an open arm.
"Head Dip" = An exploratory forward head/shoulder movement over the side of an open arm and down towards the floor.
"Protected head dips" = Exploratory forward head/shoulder movement over the side of a closed arm and down towards the floor.
"Stretch-attend posture" = An exploratory flat body posture where the mouse stretches forward and then retracts to original position without moving forward.

Measurement of Ataxic Actions

Possible ataxic effects of gabapentin were studied in control animals (i.e., not treated with ethanol) by the rotorod method. Mice were placed on a rod rotating at 4.5 rpm, and the time they remained on the rod was measured automatically. A cut-off time of 180 seconds was used in all experiments. Before the acute drug injections, all mice were tested on the rotorod to ensure that they stayed on for 180 seconds (a very small number did not do so and were excluded from the studies). Measurements were made for 60 minutes, at 10-minute intervals, after the acute administration of the drug under test. Eight mice were used in each treatment group.

Locomotor Activity

The effects of gabapentin in control animals were also tested on locomotor activity to determine the selectivity of the effects in the withdrawal studies. Mice were injected with gabapentin solution or saline and placed immediately in activity test cages crossed by infra-red beams. The number of infra-red beam breaks was measured every 5 minutes for the next 30 minutes. Rearing activity was measured by a similar set of infrared beams situated 4 cm above the cage floor.

Statistical Analysis

The results of the handling response ratings were compared by nonparametric two-way analysis of variance, designed for repeat measures on the same animal. The results of the area under the curve calculations were compared by the Mann-Whitney U-test. The convulsion incidence was analyzed by Fisher's exact probability test. The measurements from the elevated plus maze were subjected to one-way analysis of variance, followed by a Bonuferroni multiple comparison test, comparing all groups to the control group which received saline injections, and also comparing both ethanol treated groups which received gabapentin to the ethanol treated group which received saline. The ataxia measurements were analyzed by the Mann-Whitney U-test and the locomotor activity by Student's t-test.

RESULTS

Handling Response

The ratings of behavior in response to gentle handling showed the expected increase following withdrawal from the ethanol treatment. Gabapentin (GP), at 100 mg/kg (FIG. 2a), significantly reduced this increase in ratings when the results were compared over the 12-hour testing period (p<0.001). The effect of this dose of gabapentin showed a marked reduction in handling scores for around 4 hours. This time period was therefore used in later analysis to examine the area under the handling curve with each dose of the drug. The effects of lower doses of gabapentin were not significant over the 12-hour period of measurement, but when the areas under the curve were calculated for the first 4 hours of the study (FIG. 2b), significant effects of the 20- and 50-mg/kg doses were seen (p<0.05), as well as the 100-mg/kg dose (p<0.01).

Audiogenic Seizures

At the 8-hour time interval, 50 and 100 mg/kg gabapentin decreased the convulsion incidence after the audiogenic stimulus, with the 100-mg/kg dose reaching statistical significance (p<0.05). There was no effect of the lower doses (Table 4). No effect was seen of any of the doses tested at 12 hours from the end of the ethanol treatment (data not shown).

TABLE 4

The Effect of Gabapentin on Audiogenic Convulsions Measured 8 Hours From Ethanol Withdrawal

| Chronic Treatment | Acute Injection | Percentage of Group Showing Clonic Convulsions |
|---|---|---|
| Control Diet | Saline | 0 |
| Ethanol Diet | Saline | 80* p < 0.05 c.f. Control/Saline group |
| Ethanol Diet | Gabapentin 5 mg/kg | 92 |
| Ethanol Diet | Gabapentin 20 mg/kg | 70 |
| Ethanol Diet | Gabapentin 50 mg/kg | 40 |
| Ethanol Diet | Gabapentin 100 mg/kg | 30 p < 0.01 c.f. Ethanol/Saline group |

Elevated Plus Maze

Figure 3A:
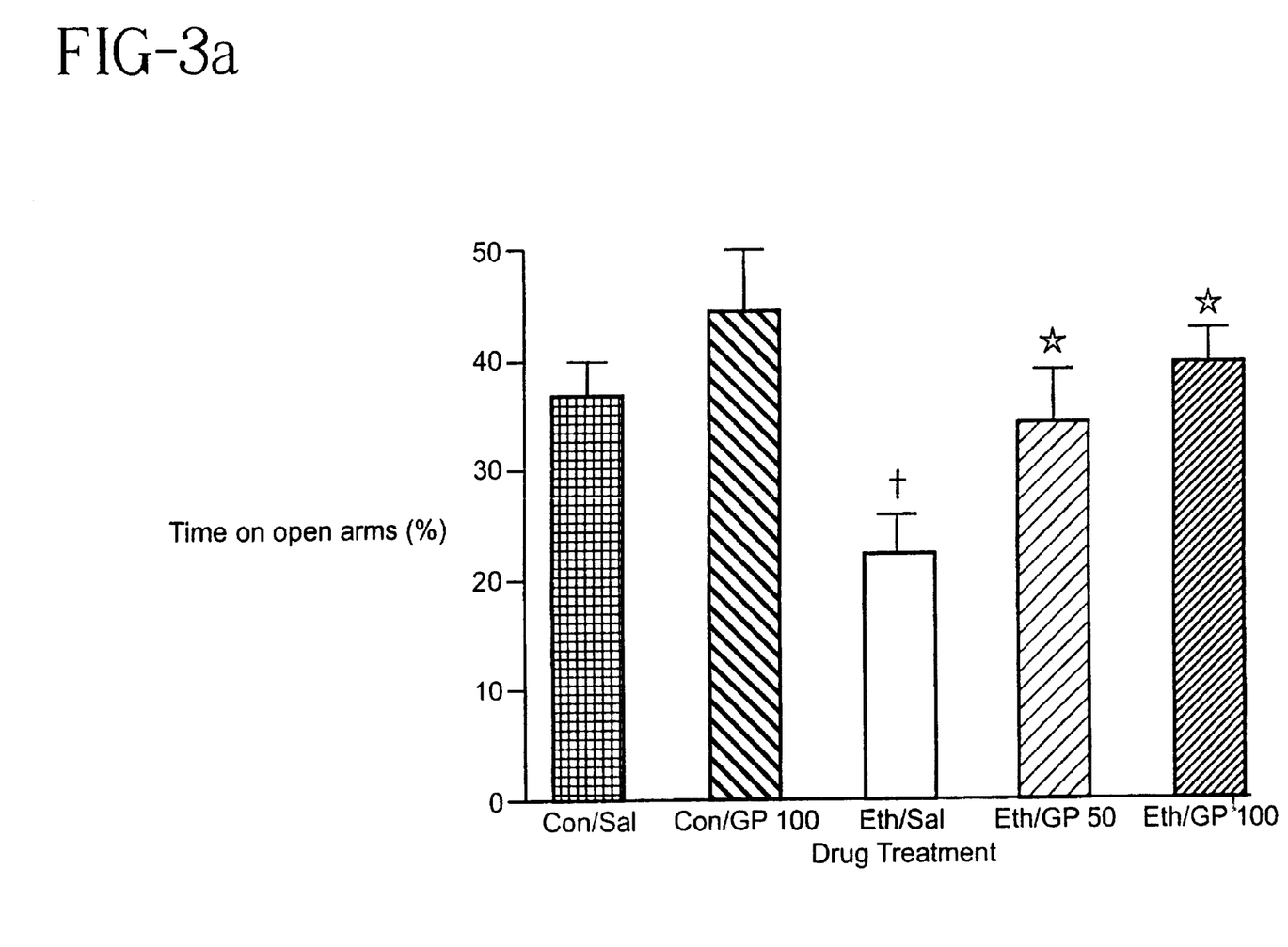
FIG. 3 shows the effect of gabapentin on memory and drowsiness in animals receiving chronic ethanol treatment.

The most prominent effect of ethanol withdrawal in this test was a decrease in the percentage time spent on the open arms of the maze (FIG. 3a, $F(4,50)=5.12$, $p<0.002$). Gabapentin decreased this effect at both 50 and 100 mg/kg. The p values were p<0.05 for the 50-mg/kg dose and p<0.01 for 100 mg/kg, for comparison with saline administration in both cases.

Figure 3B:
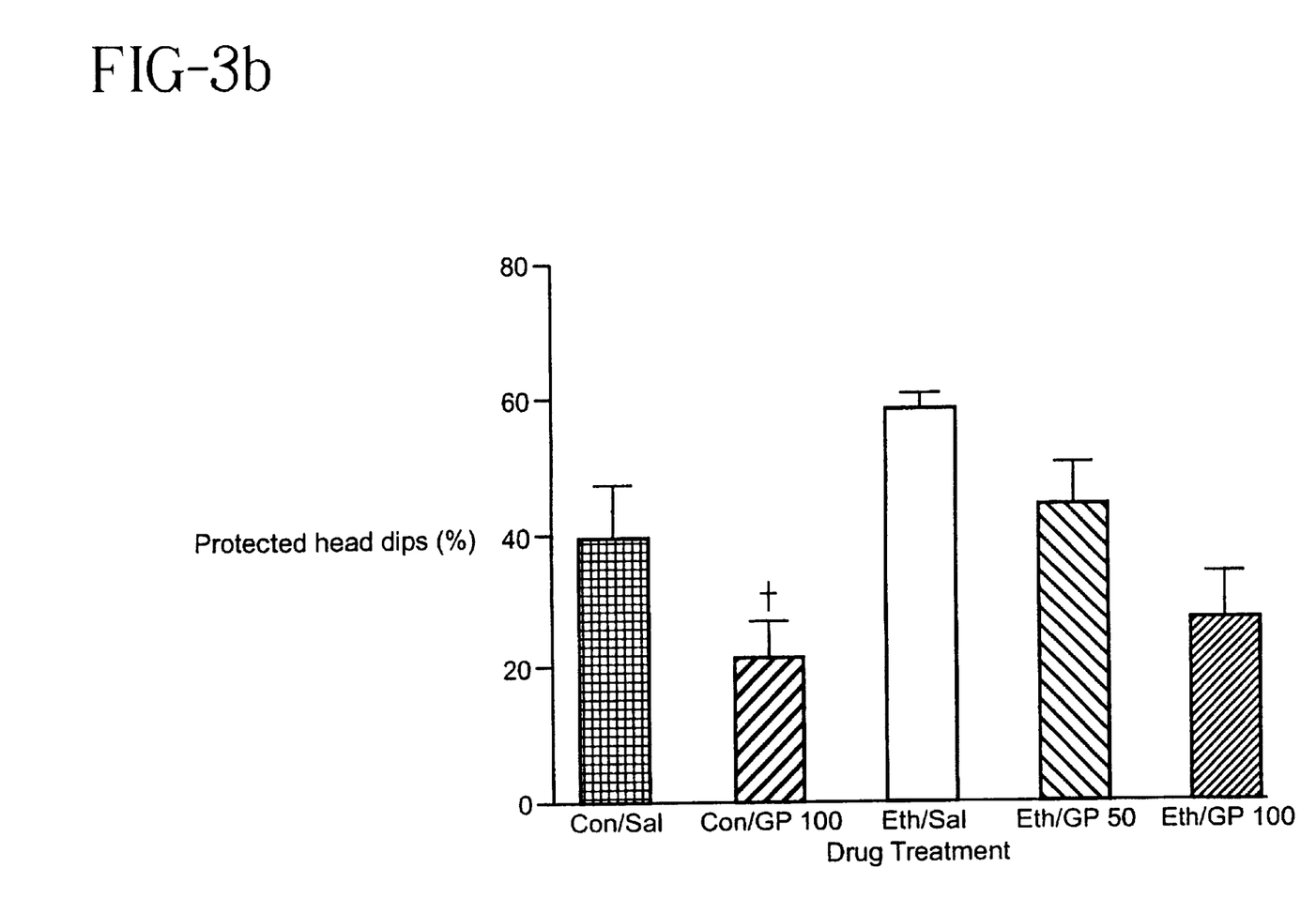

Mice undergoing ethanol withdrawal also showed a significant increase in head dips from the closed arms (protected head dips). This effect was significantly reduced by gabapentin at 100 mg/kg (p<0.01 compared with the effects of saline), as illustrated in FIG. 3b ($F(4,50)=6.53$, $p<0.001$). In control animals, the number of protected head dips was significantly decreased by gabapentin at 100 mg/kg (p<0.05, compared with control values after saline administration). Although the mean time on the open arms was increased in control animals after this dose of gabapentin, this was not significantly different from controls with saline.

EXAMPLE 5

LPS-Colonic Hypersensitivity Assay

The GABA analogs also have been evaluated for their ability to control and treat gastrointestinal disorders characterized as IBD and IBS. The assay utilized to evaluate the GABA analogs measures the effects of compound on lipopolysaccharide-induced delayed rectal allodynia in rats. Intraperitoneal (IP) injections of the endotoxin lipopolysaccharide (LPS) are known to induce long-lasting hyperalgesia in somatic pain models. The following assay LPS-colonic hypersensitivity assay was designed to evaluate the effect of IP injections of LPS on pain visceral threshold in an experimental model of rectal distension.

Animal Preparation

Male Wistar rats weighing 250 to 350 g were surgically prepared for electromyography, according to a standard technique. Rats were anesthetized by i.p. injection of acepromazine and ketamine (Imalgene 1000, Rhône-Mérieux, Lyon, France) at doses of 0.6 and 120 mg/kg, respectively. Two groups of four electrodes of nichrome wire (60 cm length and 80 μm diameter) were implanted bilaterally in the abdominal external oblique musculature just superior to the inguinal ligament. Electrodes were exteriorized on the back of the neck and protected by a glass tube attached to the skin. Animals were individually housed in polypropylene cages and kept in a temperature-controlled room (21° C.). They were allowed free access to water and food (UAR pellets, Epinay, France).

Electromyographic Recording

Electromyographic recording began 5 days after surgery. The electrical activity of abdominal striated muscles was recorded with an electroencephalo-graph machine (Mini VIII, Alvar, Paris, France) using a short-time constant (0.03 sec) to remove low-frequency signals (<3 Hz) and a paper speed of 3.6 cm/minute.

Balloon Distension Procedure

Rats were placed in plastic tunnels (6 cm diameter; 25 cm length) where they could not move, escape or turn around, in order to prevent damage to the balloon. They are accustomized to this procedure for 3 or 4 days before rectal distension (RD) in order to minimize stress reaction during experiments. The animals were determined to be accustomed to the plastic tunnel using two criteria: (i) a behavioral component: when the animals tried to escape or turn around no more than one time per 5 minutes, (ii) the abdominal basal activity: when abdominal striated muscles exhibited less than five abdominal contractions per 5 minutes in the absence of distension. The balloon used for distension was an arterial embolectomy catheter (Fogarty, Edwards Laboratories, Inc., Santa Ana, USA). Rectal distension (RD) was performed by insertion of the balloon (2-mm diameter; 2-cm long) in the rectum, at 1 cm of the anus, the catheter being fixed at the tail. It was inflated progressively by steps of 0.4 mL, from 0 to 1.6 mL, each step of inflation lasting 5 minutes. To detect possible leakage, the volume of water introduced in the balloon was checked by complete removal with a syringe at the end of the distension period.

Experimental Protocol

In a first series of experiments, a group of 8 rats were submitted to gradual rectal distention. The animals were previously (30 minutes) treated by gabapentin at doses of 30 and 100 mg/kg IP or its vehicle (NaCl 9% aqueous).

In a second series of experiments, the same group of 8 rats received IP lipopolysaccharide (*E Coli*, serotype 0111:B4) or its vehicle, at a dose of 1 mg/kg IP, 1 hour after a control rectal distension. Then, RD was performed 12 hours after LPS injection and was preceded (30 minutes) by IP administration of gabapentin (30 mg/kg) or its vehicle (0.3 mL/rat).

Drugs

LPS was dissolved in saline (NaCl 9%). Intraperitoneal injection of vehicle was given in a volume of 0.3 mL. LPS was purchased from Sigma-Aldrich (St. Quentin Fallavier, France).

Statistical Analysis

Statistical analysis of the number of abdominal contractions occurring during each 5-minute period during RD was performed by one-way ANOVA followed by Student's paired t-test. Values were expressed as the mean±SEM, and differences were considered significant for p<0.05.

The results are presented in Tables 5 and 6, and establish that gabapentin is effective in reducing lower gastrointestinal disorders such as IBS.

TABLE 5

Effect of Gabapentin on Abdominal Response Induced by Rectal Distension (Number of abdominal contractions/5 minutes; mean ± SEM, n = 7-8, *p < 0.05, **p < 0.01, significantly different from vehicle; n % of reduction vs vehicle)

| Volume of Distension | Vehicle (0.3 mL/rat) | Gabapentin (30 mg/kg) | Vehicle (0.3 mL/rat) | Gabapentin (100 mg/kg) |
|---|---|---|---|---|
| 0.4 mL | 4.4 ± 1.6 | 5.0 ± 2.1 | 3.9 ± 1.8 | 2.0 ± 1.4 |
| 0.8 mL | 19.1 ± 2.8 | 10.6 ± 3.4** (−45%) | 19.6 ± 2.3 | 7.6 ± 3.4** (−61.2%) |
| 1.2 mL | 23.4 ± 2.6 | 16.1 ± 2.3* (−31.2%) | 19.1 ± 2.3 | 16.7 ± 2.9 |

TABLE 6

Effect of Gabapentin on LPS-Induced Delayed (12 Hours) Allodynia (Number of abdominal contractions/5 minutes; mean, ±SEM, n = 7-8, +p < 0.001, significantly different from "LPS/vehicle" value; n % of reduction vs "LPS/vehicle")

| Volume of Distension | LPS (1 mg/kg) + Vehicle (0.3 mL/rat) | LPS (1 mg/kg) + Gabapentin (3.0 mg/kg) |
|---|---|---|
| 0.4 mL | 9.7 ± 1.0 | 0.7 ± 0.5 + (−92.8%) |
| 0.8 mL | 11.7 ± 1.2 | 11.9 ± 0.8 |
| 1.2 mL | 23.5 ± 2.2 | 16.3 ± 3.2 |

The foregoing experiment was carried out with the GABA-analog pregabalin. Pregabalin, at 30 mg/kg, reduced the number of cramps at both distension volumes of 0.4 and 0.8 mL. When injected 120 minutes before rectal distension, pregabalin, at both 10 and 30 mg/kg, had a similar effect at all distension volumes. LPS enhanced the number of abdominal contractions at the volume of 0.4 mL (9.7±1.0 vs. 3.7±1.0) 12 hours after its administration. This effect was suppressed when animals received pregabalin (1.8±0.9 vs. 9.7±1.0) at 30 mg/kg 30 minutes prior to rectal distension. These results establish that pregabalin is effective in reducing basal rectal sensitivity and in blocking LPS-induced rectal allodynia in rats.

EXAMPLE 6

TNBS-Induced Allodynia

GABA analogs were evaluated in rats suffering from chronic visceral allodynia induced by trinitrobenzene sulfonic acid (TNBS). Injections of TNBS into the colon of animals have been found to induce chronic colitis. In humans, digestive disorders are often associated with visceral pain. In these pathologies, the visceral pain threshold is decreased, indicating a visceral hypersensitivity. Consequently, the following study was designed to evaluate the effect of injection of TNBS into the colon on visceral pain threshold in an experimental model of colonic distension.

Male Sprague-Dawley rats weighing 340 to 400 g were used in the study. The animals were housed three per cage in a regulated environment (20±1° C., 50±5% humidity, with light 8:00 AM to 8:00 PM). Under anethesia (ketamine 80 mg/kg i.p.; acepromazin 12 mg/kg i.p.), TNBS (50 mg/kg), or saline (1.5 mL/kg) was injected into the proximal colon (1 cm from the cecum). After the surgery, animals were individually housed in the regulated environment.

A balloon catheter (5–6 cm length) was inserted through the anus into the colon and kept in position (tip of balloon 5 cm from the anus) by taping the catheter to the base of the tail. The balloon was progressively inflated by step of 5 mm Hg, from 0 to 75 mm Hg, each step of inflation lasting 30 seconds. Each cycle of colonic distension was controlled by a standard barostat. The threshold corresponds to the pressure which produced the first abdominal contraction, at which time the cycle of distension was discontinued. To determine the colonic threshold, four cycles of distension were performed on the same animal.

In a first series of experiments, a group of eight rats treated with saline were subjected to a colonic distension session.

In a second series, a group of eight rats treated with TNBS were subjected to a colonic distension session.

In a third series, a group of eight rats treated with TNBS received a subcutaneous (sc) injection of gabapentin or CI-1008 30 minutes prior to initiation of the colonic distension cycle.

All test compounds were dissolved in saline except TNBS. TNBS was dissolved in EtOH 30% (w/v). Subcutaneous injection of vehicle was given in a volume of 2 mg/kg.

Statistical significance between each group was determined using a one-way ANOVA followed by Student's unpaired t-test. Differences were considered statistically significant at p<0.05.

Pain threshold (pressure of distension inducing the first abdominal contraction) after distal colonic distension was determined at Day 7 in two groups of awake rats: control animals and TNBS-treated animals. A significant decrease in the pain threshold was observed in TNBS-treated animals. Inflammatory parameters (colon weight, area of hyperemia and necrosis and colonic myeloperoxidase content) were measured in the proximal colon at Day 7 after TNBS treatment. All the parameters were significantly increased except the area of necrosis.

Figure 4:
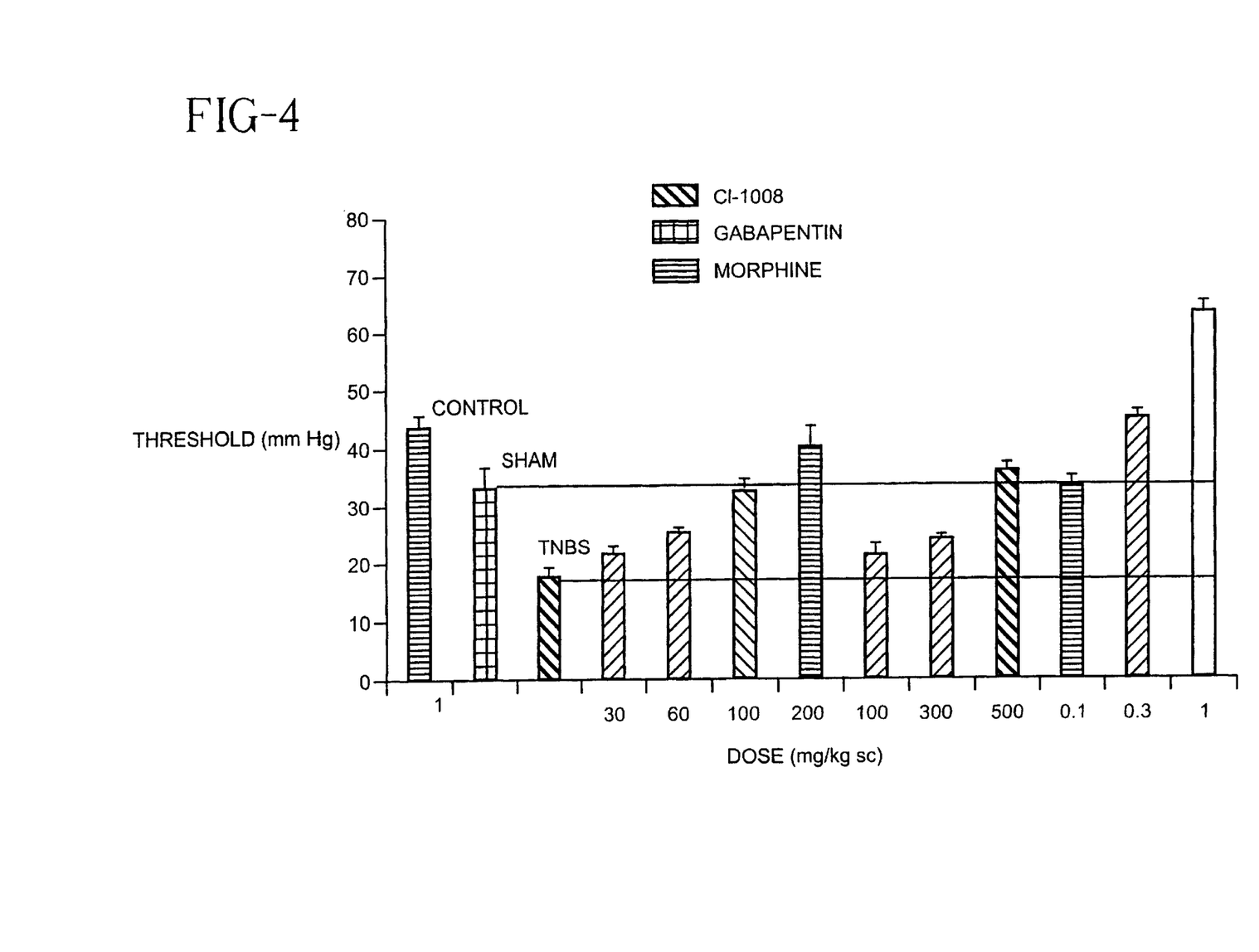
FIG. 4 shows the effects of gabapentin, CI-1008 (pregabalin), and morphine on colonic allodynia.

Gabapentin (100, 300, and 500 mg/kg sc) and CI-1008 (30, 60, 100, and 200 mg/kg sc) were administered 30 minutes before colonic distension and measurement of the inflammatory parameters. Gabapentin inhibited in a dose-related manner the TNBS-induced colonic allodynia. At 500 mg/kg sc, gabapentin completely blocked the effect of TNBS on colonic pain. CI-1008 also showed a dose-related inhibition of the decrease in pain threshold. At 100 mg/kg, CI-1008 completely suppressed the allodynia induced by TNBS. Morphine (0.1 mg/kg sc) completely suppressed the TNBS-induced decrease in pain threshold after colonic distension (FIG. 4). In contrast, neither gabapentin nor CI-1008 inhibited the colonic inflammatory effect of TNBS in these experimental conditions.

Figure 5:
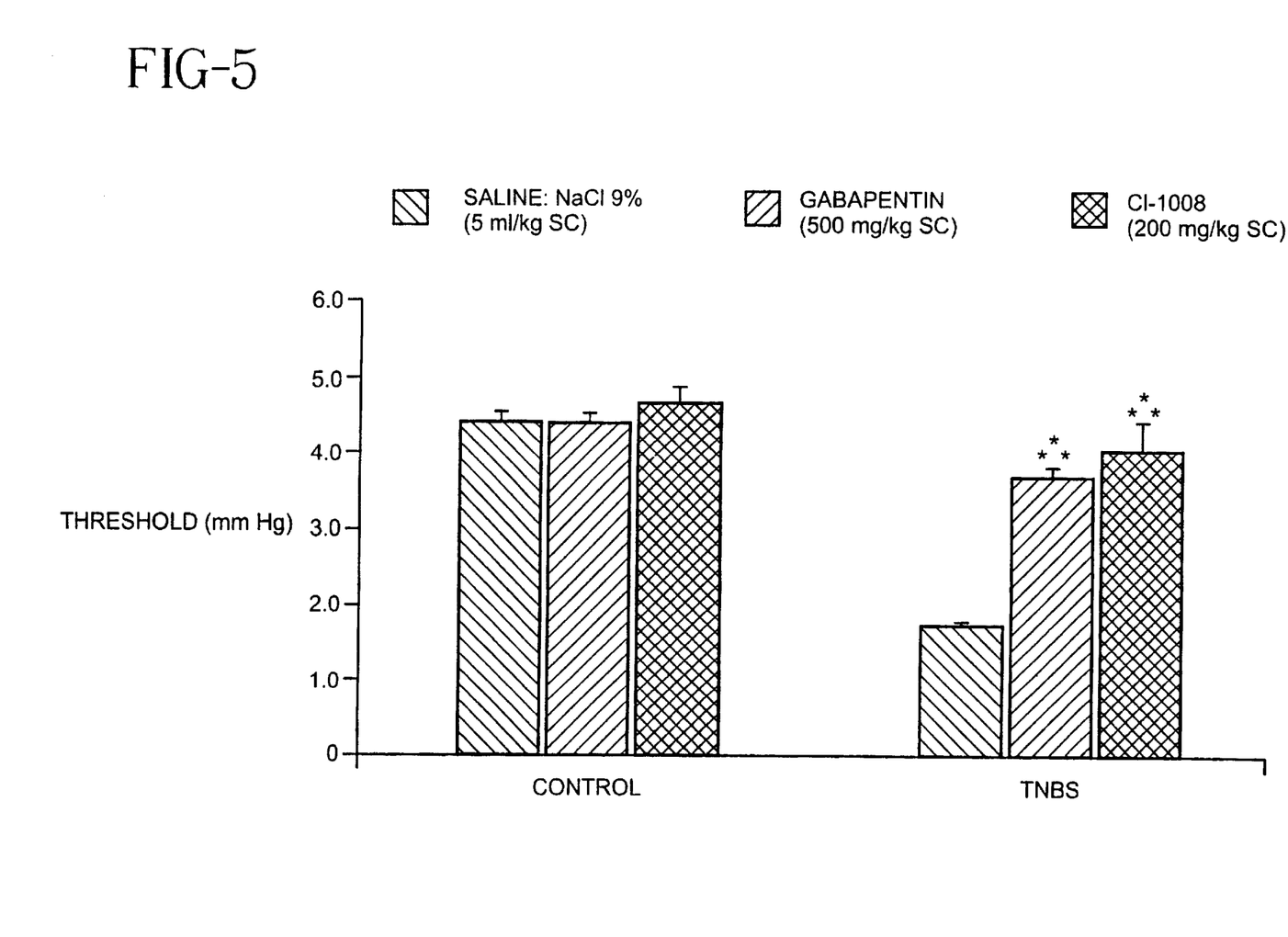
FIG. 5 shows the effects of gabapentin and CI-1008 on colonic pain threshold in rats.

In normal conditions (control animals), morphine (0.3 mg/kg sc) significantly increased the colonic pain threshold while, in the same conditions, neither gabapentin (500 mg/kg sc) nor CI-1008 (200 mg/kg sc) modified the colonic pain threshold (FIG. 5). The results are further shown in Tables 7 and 8.

TABLE 7

Effect of CI-1008, Gabapentin, and Morphine on TNBS-Induced Chronic Colonic Allodynia in Rats

| Treatment | Colonic Threshold (mm Hg) | | SEM | n | p |
|---|---|---|---|---|---|
| Control | 43.39 | ± | 1.98 | 8 | |
| Sham | 33.44 | ± | 3.25 | 8 | * |

TABLE 7-continued

Effect of CI-1008, Gabapentin, and Morphine on TNBS-Induced Chronic Colonic Allodynia in Rats

| Treatment | Colonic Threshold (mm Hg) | | SEM | n | p |
|---|---|---|---|---|---|
| TNBS | 17.81 | ± | 1.27 | 8 | *** |
| CI-1008 | | | | | |
| 30 mg/kg sc | 21.72 | ± | 1.51 | 8 | ? |
| 60 mg/kg sc | 25.47 | ± | 1.03 | 8 | ?? |
| 100 mg/kg sc | 33.13 | ± | 1.83 | 8 | ??? |
| 200 mg/kg sc | 40.47 | ± | 3.75 | 8 | ??? |
| Gabapentin | | | | | |
| 100 mg/kg sc | 22.03 | ± | 2.23 | 8 | |
| 300 mg/kg sc | 24.69 | ± | 1.27 | 8 | ? |
| 500 mg/kg sc | 36.88 | ± | 1.46 | 8 | ??? |
| Morphine | | | | | |
| 0.1 mg/kg sc | 34.22 | ± | 1.72 | 8 | ??? |
| 0.3 mg/kg sc | 46.09 | ± | 1.43 | 8 | ??? |
| 1 mg/kg sc | 64.84 | ± | 1.88 | 8 | ??? |

\* = $p < 0.05$, \*\* = $p < 0.01$, and \*\*\* = $p < 0.001$ vs control.
? = $p < 0.05$, ?? = $p < 0.01$, and ??? = $p < 0.001$ vs TNBS.

TABLE 8

Effect of CI-1008 and Gabapentin on Colonic Threshold in Normal Rats

| Treatment | Colonic Threshold (mm Hg) | | SEM | n | p |
|---|---|---|---|---|---|
| Control | 43.33 | ± | 1.23 | 6 | |
| CI-1008 200 mg/kg sc | 46.41 | ± | 2.26 | 8 | NS |
| Gabapentin 500 mg/kg sc | 43.75 | ± | 1.44 | 6 | NS |

NS = Not significant vs control.

The foregoing data establish that GABA analogs such as gabapentin and CI-1008 suppress TNBS-induced colonic allodynia, and are therefore effective in abnormal colonic hypersensitivity reflecting the chronic pain in IBS.

EXAMPLE 7

Formalin-Induced Inflammatory Colonic Pain

The GABA analogs were evaluated in another model to determine their effect on inflammatory visceral pain, including pancreatitis and intestinal cystitis.

Administration of formalin into the wall of the rat colon causes acute inflammation and visceral pain. The aim of this study was to evaluate the antinociceptive activity of gabapentin and CI-1008 in visceral pain induced by colonic intrapariental injection of formalin.

Adult female Sprague-Dawley rats weighing 240 to 260 g were used in the study. The animals were housed three per cage in a regulated environment (20±1° C., 50±5% humidity, with light 8:00 AM to 8:00 PM) prior to use in the test.

Each test animal was placed in a transparent plastic cage (27×43×28 cm) with a layer of wood shavings on the floor. Drinking water was available. Cages were placed in such a way that visual interaction between animals was avoided. A mirror was positioned behind each cage to improve the recording of behaviors. Each animal was initially allowed 20 minutes to get used to its surroundings. Anesthesia was then achieved by using isofurane (starting 4%, then 1.5% in a mixture of 2:3 nitrous oxide and 1:3 oxygen). The animal was suspended by its tail, the rectum was gently emptied with a cotton-capped stalk, and a coloscope was inserted through the anus. This designed endoscope has a lateral slot that allows for puncture of the intestinal wall under visual control, using a 51-mm-long needle (26 ga), at about 35 mm from the anal margin. Injected solutions were either 50 μL 5% aq. formalin (v/v), or the same volume of isotonic saline. Animals were allowed to recover from anesthesia as soon as the injection was completed (about 1 minute), and the observation period was started and continued for 2 hours. Thirty minutes after the end of the observation test, an IV injection of Evans Blue (1%) was administered, and 30 minutes later the animal was sacrificed. The abdomen was opened. The injection site and the zone of diffusion of Evans Blue were recorded by image analysis software. Data from rats in which the spread of the dye was not restricted to the sigmoid wall were discarded.

As listed in increasing order of pain intensity, these behaviors were: (i) abdominal licking and nibbling (L), (ii) body stretching, i.e., backward extension of the hind limbs (B), (iii) contraction of the flanks, sometimes evolving to a stretching attitude (C), and (iv) whole body contraction, the rat standing with its back curved, occasionally further graded according to the duration of the given episode: $W_1$ for less than 30 seconds, $W_2$ between 30 seconds and 1 minute, and $W_3$ for more than 1 minute. Behaviors were recorded for each animal throughout the 2-hour test on individual charts. A pain score (S) was then calculated for each of the successive 15-minute periods, using the following formula:

$$S = 1L + 2B + 3C + 4W_1 + 5W_2 + 6W_3$$

whereby the pain score was proportional to (i) the number of episodes of each selected behavior, and (ii) the coefficient, from 1 to 6, attributed to the given behaviors.

All compounds were dissolved in saline. Subcutaneous injection of vehicle was given in a volume of 2.5 mg/kg. Formalin was purchased from Prolabo.

Statistical significance between each group was determined by using a one-way ANOVA followed by Student's unpaired t-test. Differences were considered statistically significant at $p < 0.05$.

Hyperalgesia is induced by intramural injection of formalin (5%, 50 μL/rat) into the colonic wall in unfasted female Sprague-Dawley rats. Gabapentin and CI-1008 were tested at 100, 300, 500 and 100, 200 mg/kg sc, respectively. Gabapentin and CI-1008 significantly and dose-dependently decreased the pain score induced by intracolonic formalin. The maximal inhibitory effect was observed after 500 mg/kg of gabapentin and 200 mg/kg of CI-1008. The results are presented in Table 9.

This study establishes that GABA analogs exhibit an antinociceptive effect on intra-colonic formalin-induced pain, and thus are effective in treating IBD and IBS, and visceral pain, including pancreatitis and intestinal cystitis.

TABLE 9

Effect of Subcutaneous Injection of Gabapentin and CI-1008 on Inflammatory Colonic Pain Induced by Intramural Injection of Formalin 5%

| Treatment | % Antinociception | | SEM | n | p |
|---|---|---|---|---|---|
| CI-1008 | | | | | |
| 100 mg/kg sc | 18.55 | ± | 7.41 | 7 | *** |
| 200 mg/kg sc | 70.81 | ± | 7.47 | 6 | *** |
| Gabapentin | | | | | |
| 0.3 mg/kg sc | −7.73 | ± | 10.43 | 3 | NS |
| 100 mg/kg sc | 13.62 | ± | 12.65 | 9 | NS |
| 300 mg/kg sc | 55.07 | ± | 9.98 | 6 | *** |
| 500 mg/kg sc | 88.01 | ± | 16.96 | 6 | *** |

*** =
NS = Not significant vs control.

The following examples further illustrate compositions provided by the invention which contain a GABA analog in combination with an NSAID.

EXAMPLE 8

| Tablet Formulation | |
|---|---|
| Naproxen sodium | 200 mg |
| Gabapentin | 300 mg |
| Magnesium stearate | 20 mg |
| Microcrystalline cellulose | 100 mg |
| Povidone | 100 mg |
| Talc | 50 mg |

The ingredients are blended to uniformity and pressed into a tablet. The tablets are administered from 1 to 3 times a day for treatment of inflammatory conditions such as rheumatoid arthritis, ankylosing spondylitis, osteoarthritis, bursitis, tendinitis, and acute gouty arthritis.

EXAMPLE 9

| Capsule Formulation | |
|---|---|
| Fenoprofen calcium, USP | 150 mg |
| Pregabalin | 50 mg |
| Cellulose | 100 mg |
| Gelatin | 50 mg |
| Titanium dioxide | 10 mg |
| Cornstarch | 50 mg |

Figure 6:
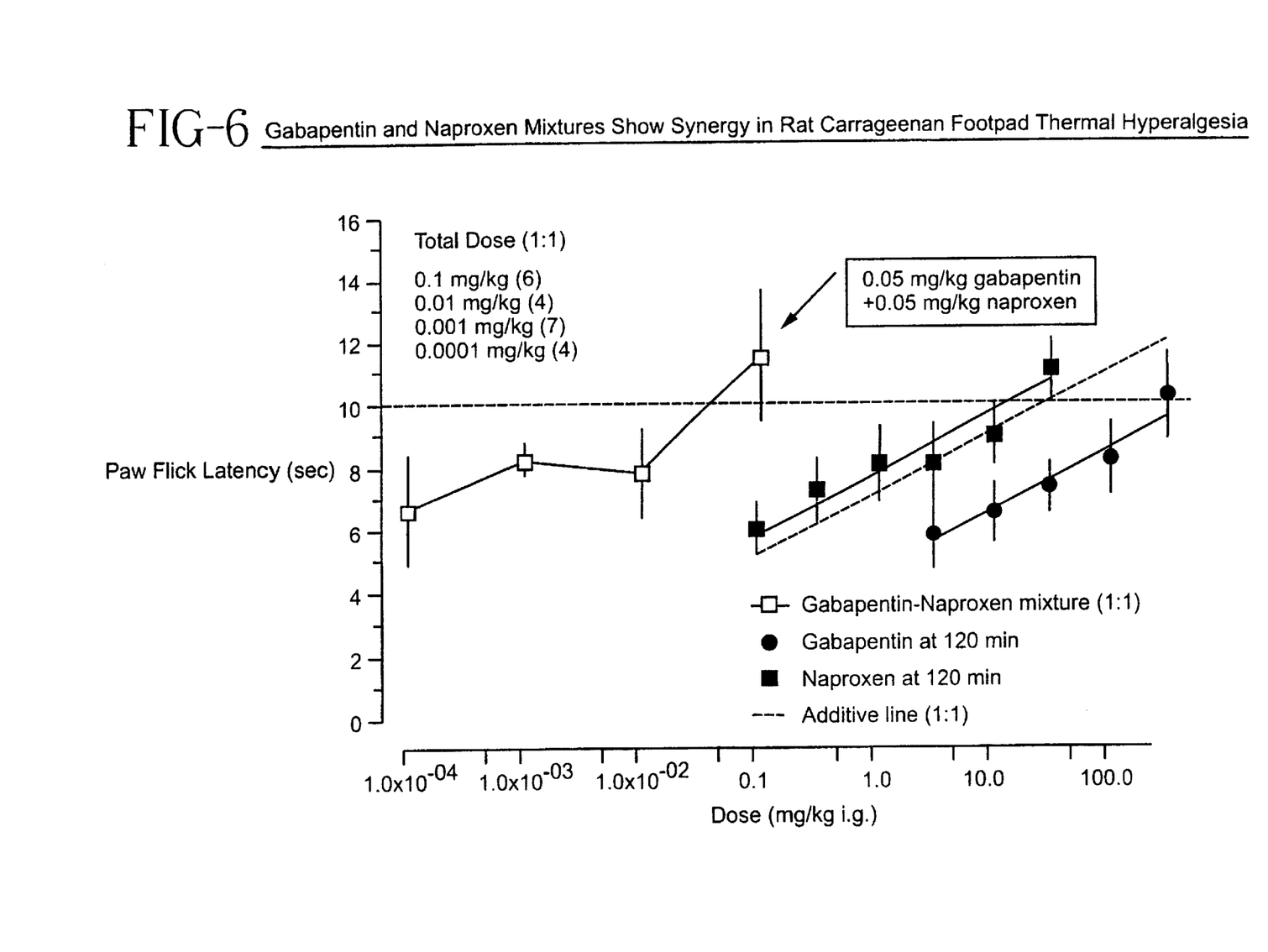
FIGS. 6 and 7 show synergistic effects of gabapentin and naproxen mixtures.
Figure 7:
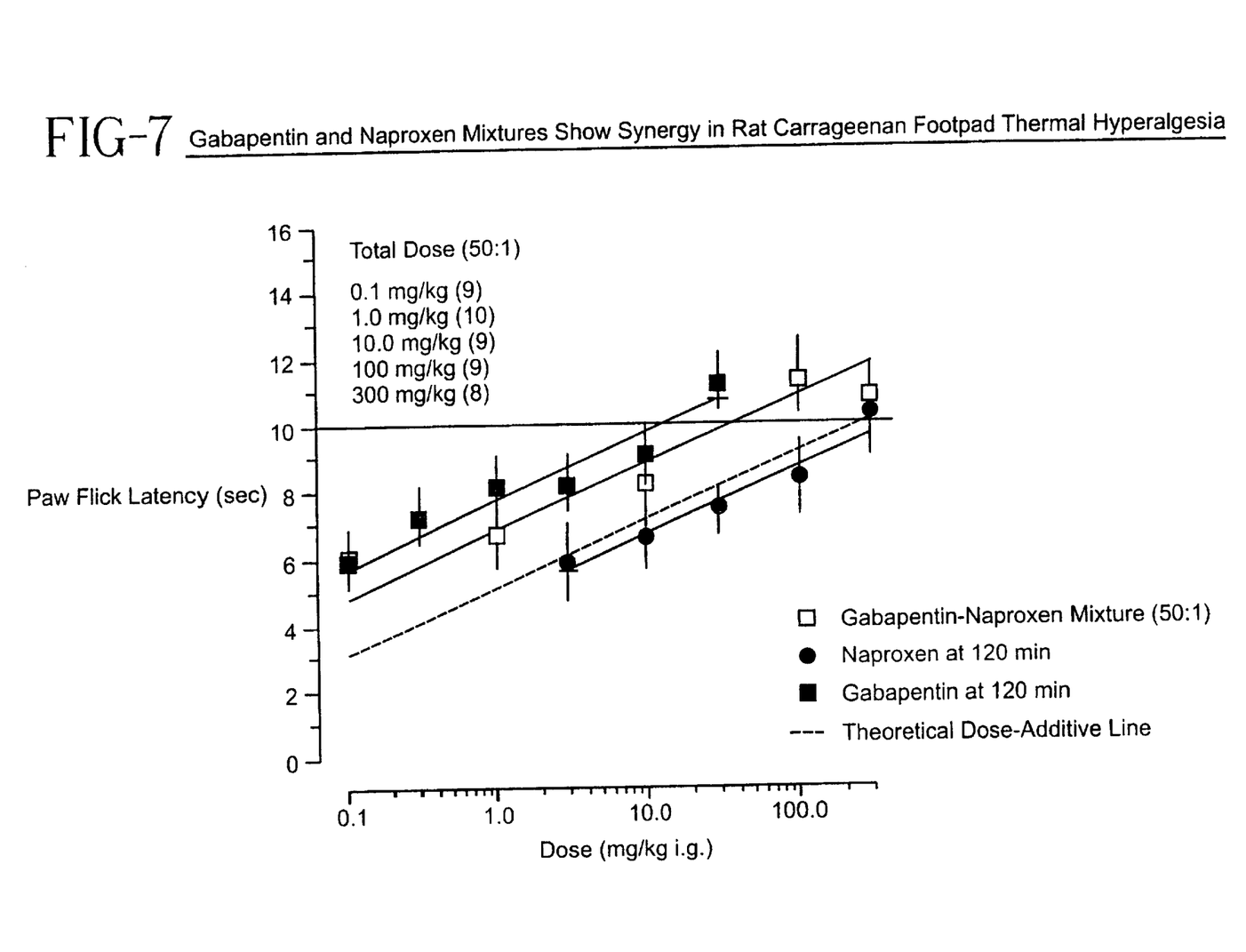

The ingredients are blended to uniformity and placed into a gelatin capsule. The capsules are administered from 1 to 4 times a day for treatment of rheumatoid arthritis and osteoarthritis. The combinations provided by this invention comprise an NSAID (eg, naproxen or meclofenamic acid) and a GABA analog (eg, pregabalin or gabapentin). Such combinations have been shown to be synergistic in their ability to treat pain. For example, gabapentin and naproxen sodium were combined in synergistic amounts and evaluated in a standard rat carrageenan footpad thermal hyperalgesia assay. This assay utilizes an extract of seaweed (carrageenan) that, when injected into the footpad of test animals, causes a sterile inflammation, thereby lowering the pain threshold. Analgesic agents, including GABA analogs such as gabapentin, raise the pain threshold back to normal, thereby enabling the animal to tolerate an external source of pain for a longer period of time relative to untreated control animals. Several fixed combinations of gabapentin and naproxen sodium, ranging in concentrations of about 50 parts by weight of GABA analog to 1 part by weight of NSAID, to 1:1 combinations, were evaluated in the foregoing assay. The results are shown in FIG. 6 (for fixed 1:1 combinations at various dosages) and in FIG. 7 (for fixed 50:1 combinations at various dosages). The data establish that the combinations of a GABA analog and an NSAID are synergistic in their ability to relieve acute and chronic pain and to induce analgesia.

What is claimed is:

1. A method for preventing and treating gastrointestinal damage and disorders comprising administering to a subject in need of treatment an effective amount of a GABA analog.

2. A method according to claim 1 employing a compound of Formula I wherein $R_1$ is hydrogen or lower alkyl and n is an integer of from 4 to 6, and the pharmaceutically acceptable salts thereof.

3. The method according to claim 2 employing gabapentin.

4. The method according to claim 1 employing a compound selected from (1-aminomethyl-3-methylcyclohexyl)acetic acid, (1-aminomethyl-3-methylcyclopentyl)acetic acid, and (1-aminomethyl-3,4-dimethylcyclopentyl)acetic acid.

5. A method according to claim 1 employing a compound of Formula II wherein $R_1$ is a straight or branched alkyl of from 1 to 6 carbon atoms, phenyl, or cycloalkyl of from 3 to 6 carbon atoms;

$R_2$ is hydrogen or methyl; and $R_3$ is hydrogen, methyl, or carboxyl, and the pharmaceutically acceptable salts thereof.

6. The method according to claim 5 employing pregabalin.

7. The method according to claim 5 employing R-(3)-(aminomethyl)-5-methyl-hexanoic acid.

8. The method according to claim 5 employing 3-(1-aminoethyl)-5-methylhexanoic acid.

9. The method according to claim 1 wherein the gastrointestinal damage is in a subject who is receiving or will receive NSIAD therapy or alcohol.

10. The method according to claim 1 wherein the gastrointestinal damage is characterized as inflammatory bowel disorder or irritable bowel syndrome.

11. The method according to claim 1 wherein the condition treated is selected from Crohn's disease, ileitis, ischemic bowel disease, dyspepsia, and ulcerative colitis.

12. A method for treating ethanol withdrawal syndrome in a mammal in need of treatment comprising administering an effective amount of a GABA analog.

13. A method according to claim 12 employing a compound of Formula I wherein $R_1$ is hydrogen or lower alkyl and n is an integer of from 4 to 6, and the pharmaceutically acceptable salts thereof.

14. The method according to claim 13 employing gabapentin.

15. A method according to claim 12 employing a compound of Formula II wherein $R_1$ is a straight or branched alkyl of from 1 to 6 carbon atoms, phenyl, or cycloalkyl of from 3 to 6 carbon atoms;

$R_2$ is hydrogen or methyl; and $R_3$ is hydrogen, methyl, or carboxyl, and the pharmaceutically acceptable salts thereof.

16. The method according to claim 15 employing pregabalin.

17. A pharmaceutical composition comprising a GABA analog and a non-steroidal anti-inflammatory drug together with a pharmaceutically acceptable excipient, carrier, or diluent therefor.

18. A composition of claim 17 wherein the GABA-analog is a compound of Formula I wherein $R_1$ is hydrogen or lower alkyl and n is an integer of from 4 to 6, and the pharmaceutically acceptable salts thereof.

19. The composition of claim 18 wherein the GABA analog is gabapentin.

20. A composition according to claim 17 wherein the GABA analog is a compound of Formula II.

21. The composition of claim 20 wherein the GABA analog is pregabalin.

22. A composition according to claim 17 wherein the non-steroidal anti-inflammatory drug is selected from sulindac, naproxen, indomethacin, mefenamic acid, diclofenac, fenoprofen, diflunisal, etodolac, ibuprofen, piroxicam, acetylsalicylic acid, oxaprozin, and bromfenac, or pharmaceutical salts thereof.

23. A composition according to claim 22 wherein the non-steroidal anti-inflammatory drug is selected from naproxen sodium, ibuprofen, or indomethacin.

24. A composition of claim 23 comprised of naproxen sodium and pregabalin.

25. A composition of claim 23 comprised of naproxen sodium and gabapentin.

26. A composition of claim 23 comprising ibuprofen and pregabalin.

27. A composition of claim 23 comprising ibuprofen and gabapentin.

* * * * *

UNITED STATES PATENT AND TRADEMARK OFFICE
Certificate

Patent No. 6,127,418                                                                             Patented: October 3, 2000

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Lionel Bueno, Aussonne, France; Maria Chovet, Montrouge, France; Laurent Diop, Saclay, France; Antonio Guglietta, Ann Arbor, MI; Hilary J. Little, County Durham, United Kingdom; Michael Francis Rafferty, Ann Arbor, MI; Jiayuan Ren, Oklahoma City, OK; Charles Price Taylor, Jr., Chelsea, MI; William P. Watson, County Durham, United Kingdom; and Richard F. Harty, Oklahoma City, OK.

Signed and Sealed this Seventh day of January 2003.

RAYMOND HENLEY, III
*Primary Examiner*
Art Unit 1600